(12) United States Patent
Bugg et al.

(10) Patent No.: US 6,468,944 B1
(45) Date of Patent: *Oct. 22, 2002

(54) METHOD OF PREPARING GLYPHOSATE HERBICIDE FORMULATIONS

(76) Inventors: M. Wayne Bugg, 1521 Virginia Ave., Ellisville, MO (US) 63011; Kristin A. Arnold, 1012 N. Harrison, Kirkwood, MO (US) 63122; Randall J. White, 823 Robin Hood Dr., Miamisburg, OH (US) 45342

( * ) Notice: Subject to any disclaimer, the term of this patent is extended or adjusted under 35 U.S.C. 154(b) by 0 days.

This patent is subject to a terminal disclaimer.

(21) Appl. No.: 09/264,569

(22) Filed: Mar. 8, 1999

Related U.S. Application Data

(60) Continuation of application No. 08/790,400, filed on Jan. 29, 1997, now Pat. No. 5,994,269, which is a continuation of application No. 08/464,028, filed on Jun. 5, 1995, now abandoned, which is a division of application No. 07/638,590, filed on Jan. 8, 1991, now abandoned.

(51) Int. Cl.$^7$ .................. A01N 57/12; A01N 57/20; A01N 37/02; A01N 37/06
(52) U.S. Cl. .................. 504/127; 504/142; 504/206; 504/320; 504/358
(58) Field of Search .................. 504/127, 142, 504/206, 320, 358; 71/DIG. 1

(56) References Cited

U.S. PATENT DOCUMENTS

| | | | |
|---|---|---|---|
| 3,799,758 A | 3/1974 | Franz | 71/86 |
| 3,870,503 A | 3/1975 | Nickell | 71/106 |
| 3,977,860 A | 8/1976 | Franz | 71/86 |
| 4,134,754 A | 1/1979 | Hoffman | 71/111 |
| 4,159,901 A | 7/1979 | Beestman et al. | 71/86 |
| 4,395,275 A | 7/1983 | Purdum | 71/87 |
| 4,405,531 A | 9/1983 | Franz | 260/501.12 |
| 4,411,693 A | 10/1983 | LeClair et al. | 71/118 |
| 4,436,547 A | 3/1984 | Sampson et al. | 71/76 |
| 4,486,358 A | 12/1984 | Moser | 260/502.5 |
| 4,626,274 A | 12/1986 | Hausmann et al. | 71/93 |
| 4,840,659 A | 6/1989 | Franz | 71/86 |
| 4,894,082 A * | 1/1990 | Borrod et al. | 558/170 |
| 4,902,334 A | 2/1990 | Azuma et al. | 71/88 |
| 4,904,645 A | 2/1990 | Puritch | 514/65 |
| 4,966,728 A | 10/1990 | Hazen | 252/354 |
| 4,975,110 A | 12/1990 | Puritch et al. | 71/113 |
| 5,035,741 A | 7/1991 | Puritch et al. | 71/113 |
| 5,196,044 A | 3/1993 | Caulder et al. | 504/127 |
| 5,389,598 A * | 2/1995 | Berk et al. | 504/206 |
| 5,612,285 A * | 3/1997 | Arnold | 504/206 |
| 5,693,593 A * | 12/1997 | Arnold | 504/206 |
| 5,700,759 A * | 12/1997 | Caulder | 504/133 |
| 5,750,468 A | 5/1998 | Wright et al. | 504/206 |

FOREIGN PATENT DOCUMENTS

| | | |
|---|---|---|
| CA | 1272890 | 8/1990 |
| DE | 3247050 | 6/1984 |
| EP | 0 192 583 | 8/1986 |
| WO | WO 89/03178 | 4/1989 |
| WO | WO 90/07275 | 7/1990 |
| WO | WO 91/05472 | 5/1991 |
| WO | WO 92/07467 | 5/1992 |

OTHER PUBLICATIONS

A. J. Wells, et al., "Adjuvants, Glyphosate Efficacy and Post–Spraying Rainfall," *Plant Protection Quarterly* 4(4):158–64 (1989), abstract.

D. G. Shilling, et al., "Influence of Surfactants and Additives on Phytotoxicity of Glyphosate to Torpedograss," *Journal of Aquatic Plant Management* 28:23–27 (1990), abstract.

Grossbard et al., The Herbicide Glyphosate, 9, 10 and 140 (London, England, Butterworth & Co. Ltd., 1985).

* cited by examiner

*Primary Examiner*—John Pak
(74) *Attorney, Agent, or Firm*—Howrey Simon Arnold & White

(57) ABSTRACT

This invention relates to a novel aqueous agriculturally acceptable formulation, a process used to prepare it and a pesticidal method of using it in application to plants or weeds to kill or control plants or weeds. The formulation comprises an effective amount of N-phosphonomethylglycine or an agriculturally acceptable salt of N-phosphonomethylglycine and an effective amount of at least one $C_5$ to $C_{16}$ or preferably a $C_8$ to $C_{12}$ agriculturally acceptable fatty acid itself or in the form of an agriculturally acceptable water soluble salt or mixtures thereof. Other ingredients are optional, including surfactant(s), antifoam(s) and antimicrobial(s) or other ingredients such as pesticides including herbicides, insecticides and fungicides.

22 Claims, No Drawings

METHOD OF PREPARING GLYPHOSATE HERBICIDE FORMULATIONS

This is a continuation of application Ser. No. 08/790,400, filed Jan. 29, 1997 now U.S. Pat. No. 5,994,269 which is a continuation application of Ser. No. 08/464,028 filed Jun. 5, 1995, now abandoned; which is a divisional application of Ser. No. 07/638,590, filed Jan. 8, 1991, now abandoned.

FIELD OF THE INVENTION

This invention relates to a novel aqueous agriculturally acceptable herbicidal formulation, a process used to prepare it and a herbicidal method of using it in applying it to weeds or plants to kill and control weeds or plants.

The formulation, preferably a herbicidally efficacious formulation, comprises an effective amount of an agriculturally acceptable salt of N-phosphonomethylglycine and a herbicidally effective amount of at least one agriculturally acceptable fatty acid or a salt thereof or a mixture of fatty acids and a salt(s) thereof or a mixture of salts of a fatty acid(s) giving in an aqueous solution to be applied to plants or a desired locus a pH in a desired range. Other ingredients are optional, including surfactant(s), antifoam(s), antimicrobial(s) or one or more additional pesticides including herbicides, insecticides and fungicides. As used herein, the term "agriculturally acceptable" includes residential and industrial uses.

DESCRIPTION OF THE PRIOR ART

Glyphosate (N-phosphonomethylglycine) well-known as an effective herbicide is an organic acid, and is relatively insoluble in water. Therefore, glyphosate is normally formulated and applied as a water-soluble salt, especially as the isopropylamine salt (IPA salt).

Various formulations of glyphosate are disclosed in U.S. Pat. Nos. 4,405,531 issued to John E. Franz on Sep. 20, 1983; 3,799,580 issued to John E. Franz on Mar. 26, 1974; and 4,840,659 issued to John E. Franz on Jun. 20, 1989. These patents are incorporated herein by reference in their entirety. Roundups herbicide an aqueous concentrate comprising the IPA salt of glyphosate is sold by Monsanto Company as an aqueous concentrate formulation which is normally diluted in water prior to application.

Sharpshooter(TM) Herbicide Concentrate from Safer Inc. is said to contain fatty acid(s) as active ingredients such as those having 8 to 12 carbon atoms and mixtures thereof. It is believed used as a vegetation suppression agent.

SharpShooter(TM) is non-selective, and shows the result of its contact with weeds and unwanted vegetation in the form of necrosis, leaf burn, desiccation, wilting and the like. Typical fatty acids known to produce such symptoms are pelargonic and n-capric acid.

Pelargonic acid referred to also as nonanoic acid, nonylic acid and nonoic acid has the empirical formula $C_9H_{18}O_2$.

n-Capric acid known also as n-decanoic acid, has the empirical formula $C_{10}H_{20}O_2$.

PCT/US88/03582 (WO89/03178) of Safer, Inc. discloses a herbicidal composition and method for non-selectively controlling and retarding the growth rate and, if desired, causing extensive mortality of unwanted vegetation. The compositions consist essentially of one or more substances selected from the group consisting of aliphatic acids or their herbicidally active salts, disclosed preferably as octanoic acid, nonanoic acid, decanoic acid, n-decanoic acid, or dodecanoic acid, and an ammonium compound, preferably ammonium nitrate, sulfate or sulfanate. The composition is said to cause a plant mortality significantly in excess of the expected additive mortalities of the individual components.

U.S. Pat. No. 4,975,110 issued to George S. Puritch et al discloses an environmentally compatible herbicidal composition, consisting essentially of a herbicidally effective amount of a saturated linear monocarboxylic fatty acid selected from the group consisting of the acids caprylic, pelargonic, capric, undecanoic, lauric and mixtures thereof; and a surfactant component.

U.S. Pat. No. 3,870,503 issued to Louis G. Nickell on Mar. 11, 1975 discloses that sucrose yield of sugar-cane is increased by treating sugarcane a few weeks prior to harvest with a sugar cane ripening agent selected from the group consisting of n-valeric (pentanoic) acid and alkali metal salts or ethyl esters of an aliphatic monoacid having from one to five carbon atoms.

U.S. Pat. No. 4,134,754 issued to Otto L. Hoffmann on Jan. 16, 1979 discloses that the activity of barban is enhanced and variation of selectivity with climatic conditions is alleviated by applying to wild oats an effective amount of a composition comprising one part by weight carbon and at least four parts by weight of a polyunsaturated fatty acid exemplified by linolenic acid. The composition is preferably either dispersed in water with the aid of an emulsifier or dissolved in a mixture of water and a volatile organic solvent such as acetone.

U.S. Pat. No. 4,436,547 issued to Michael J. Sampson on Mar. 13, 1984 discloses that the effect of fungicides, herbicides, insecticides, nematocides and plant-growth regulators, is improved by co-administration of them with one or more of the following additives: carbohydrates, organic acids (particularly fatty acids and acids of the Krebs tricarboxylic acid cycle), vitamins and co-enzymes, purine and pyrimidine nucleosides and nucleotides, naturally occurring fats and oils, certain amino acids and (but not where the agricultural chemical is itself a plant-growth regulator) plant-growth regulators. The invention is said to provide compositions containing one or more of the said agricultural chemicals and one or more of the said additives and methods of improving the harvest of a given crop by applying to it one or more of the said agricultural chemicals and one or more of the additives, either simultaneously or within up to about ten days of one another.

U.S. Pat. No. 4,626,274 issued to Heinz Hausmann on Dec. 2, 1986 discloses that a known herbicide such as a urea, carboxylic acid ester, aminoacid, benzoic derivative, benzonitrile, phenol derivative, diphenyl ether, triazinone, triazinedione, heterocycle, dipyridil derivative or benzosulphonamide, is rendered more effective by being combined with a synthetic spreading agent such as a silicone oil, etc.

U.S. Pat. No. 4,966,728 issued to James L. Hazen, on Oct. 30, 1990 discloses herbicide adjuvants which are said to enhance the effectiveness of a broad spectrum of postemergent herbicides. These adjuvants preferably contain a low foaming nonionic surfactant, an anionic surfactant, a lower alkanol ester of a fatty acid, and a hydrocarbon oil component.

U.S. Pat. No. 4,902,334 issued to Azuma et al on Feb. 20, 1990 discloses a plant metabolism regulating agent comprising as an active ingredient an alpha, beta or beta, gamma-unsaturated carboxylic acid or its derivative. This concept is said to be useful for controlling the metabolism of a plant, facilitating the growth of a beneficial plant such as cereals by inhibiting the growth of undesirable plants or eradicating them, regulating the growth of a plant and dwarfing a plant.

U.S. Pat. No. 4,904,645 issued to George S. Puritch et al on Feb. 27, 1990 discloses a combination of pyrethrum and fatty acid salt material which is said to provide a stable; commercially useful and environmentally safe pesticidal formulation. The specific composition comprises an aqueous solution having a pH within the range of 7.5 to 8.8; an aqueous solution comprising about 50% by weight of monocarboxylic acids and their alkali metal salts, where the acid mixture is at least 70% oleic acid and 6% linoleic acid; a pyrethrum extract; a solvent for the pyrethrum, which is preferably a 2–6 carbon alcohol; a trace amount of an antioxidant. The composition is said to be effective against insects of at least the orders Homoptera, Coleoptera, Dermaptera, Hemiptera, and Lepidoptera, and against crustacea of the order Isopoda.

OBJECTS OF THE INVENTION

An objective of this invention is to provide an aqueous concentrate or ready to apply formulation comprising glyphosate or a water soluble salt of glyphosate and a fatty acid or a salt thereof or a mixture of fatty acids and salt thereof or a mixture of salts of the fatty acid(s) such that the early burndown symptoms on plants of the fatty acid and/or its salt or mixtures thereof are seen and the long term herbicidal control achieved by the use of the glyphosate is maintained and not sacrificed, eliminated or reduced by the contact action of the fatty acid or its water soluble salt. Enhanced shelf-stability is provided when the application pH is in the preferred range.

Without being bound by theory, it is believed that the fatty acid is the responsible moiety for providing the early contact visible symptoms on plants treated with a fatty acid salt contained in a formulation of this invention.

BRIEF DESCRIPTION OF THE INVENTION

The foregoing objects are provided in an agriculturally acceptable herbicidal composition comprising herbicidally effective amounts of each of:

a) N-phosphonomethylglycine (glyphosate) or an agriculturally acceptable water soluble salt of N-phosphonomethylglycine or a compound which metabolizes thereto and b) a fatty acid such as a $C_5$ to $C_{16}$ or preferably a $C_8$ to $C_{12}$ saturated or unsaturated, straight or branched chain fatty acid or an agriculturally acceptable salt(s) thereof or a mixture of fatty acids and salt(s) thereof or a mixture of salts of a fatty acid(s) recognizing that such fatty acids may themselves be mixtures.

A preferred composition is wherein the ratio of a) to b) is in the range from about 1:10 to about 10:1 by weight and more preferably wherein the ratio of a) to b) is in the range from about 1:5 to about 5:1 and most preferably in the range from about 1:3 to about 3:1.

Especially preferred are the mono-isopropylamine and the trimethylsulfonium salts of N-phosphonomethylglycine.

Especially preferred are the potassium salts of capric fatty acid and pelargonic fatty acid and mixtures thereof. Potassium nonanoate and potassium decanoate may be enployed.

Also disclosed is a method of killing or controlling plants where a herbicidally effective amount of the above described herbicidal composition is applied to said plants to kill or control said plants and wherein the early burndown effect of application of the fatty acid or a salt thereof can be readily seen leaving intact the longer term control opportunity which is provided by simultaneous application of glyphosate or of the glyphosate moiety in the form of a water soluble salt of glyphosate or a compound which metabolizes to glyphosate.

Also disclosed is a process for preparing herbicidal compositions of this invention wherein a base such as those providing hydroxide in water preferably an amine or alkali metal or alkaline earth metal hydroxide most preferably potassium hydroxide is employed to control the desired final adjusted pH in the range from about 6.4 to about 7.25 and preferably in the range from about 6.8 to about 7.0 to provide an improved storage stable formulation, which is ready to use or ready to dilute.

DETAILED DESCRIPTION OF THE INVENTION

The present invention relates to an agriculturally acceptable herbicidal, shelf-stable ready to use or shelf-stable aqueous concentrate formulation of N-phosphonomethylglycine or a water soluble salt of N-phosphonomethylglycine or salts or mixtures thereof, with one or more $C_5$ to $C_{16}$ or preferably $C_8$ to $C_{12}$ saturated or unsaturated, straight or branched chained fatty acid itself or in the form of a salt, salts or various mixtures thereof.

Various optional ingredients may also be employed if desired although not required. Greater or lesser amounts of those optional additiments may be employed as desired.

When the application pH of the formulation of the present invention is in the range from about 6.4 to about 7.25, and more preferably in the range from about 6.8 to about 7.0, the formulations of this invention show increased shelf-stability in that they do not experience separation such as salting out or settling out of one or more ingredients when stored for prolonged periods of time at normal room temperatures or when undergoing accelerated aging studies done at 50° C. or 60° C. or at freezing temperatures.

As used herein, the phrase "early burndown symptoms" means visible plant symptoms characteristic of the contact action of a fatty acid or a salt thereof upon the leaf of a plant when applied in an effective amount alone to the surface of a plant. Such symptoms illustratively include necrosis, leafburn, desiccation, wilting and the like as visible evidence of herbicidal effectiveness.

As used herein, the term "long term control" means a significant inhibition of regrowth which is achieved through the use of a herbicidally effective amount of glyphosate (or glyphosate salt or a mixture thereof) on a plant to be killed or controlled.

The formulation of the present invention contains at least one water-soluble salt of glyphosate or a mixture of such salts. Several processes for the preparation of glyphosate and its water soluble salts are disclosed in the patent and chemical literature, e.g., U.S. Pat. Nos. 3,977,860 and 4,486,358. Illustrative suitable water-soluble salts of glyphosate useful in the present invention are disclosed in U.S. Pat. No. 4,405,531. The isopropylamine salt of glyphosate is most preferred in the formulation, preparation of the formulation and use of the present invention.

If desired, one or more of ammonium sulfate or potassium sulfate or any other compatible active or compatible non-active ingredient may be employed as an additional ingredient(s) in a process for preparing a formulation of the present invention, in its preparation and its use.

If ammonium sulfate is used during the formulation process, the formulation is normally filtered (or optional equivalent means) to remove any insoluble particulate materials which may be present in some commercial grades of ammonium sulfate.

The concentrates and solutions of the invention may contain optional additional components, for example anti-freeze agents such as ethylene glycol and propylene glycol.

Other examples are dyes, thickening agents, anti-foam agents, for instance silicone-based anti-foam agents, and surfactants, for instance non-ionic or cationic surfactants.

Additional illustrative suitable nonionic surfactants are recited in U.S. Pat. No. 4,405,531 supra. Other suitable nonionic surfactants will be known to those skilled in the art.

Other surfactants which may be employed include alkylamine oxides, alkyl glucosides, ethoxylated or propoxylated quaternary amines and dialkylacetylene surfactants.

Particularly preferred, although optional, is an ethoxylated tallow amine surfactant having a degree of ethoxylation in the range from about 15 to about 18, mixtures thereof and the like. One such surfactant is Entry II, sold by Monsanto Company, St. Louis, Mo. USA.

The amount of surfactant optionally employed is typically in the range from about 0 to about 2 percent by weight of a ready to use formulation of a spray solution formed by dilution with water of a concentrate formulation of this invention.

The concentrates and ready to use solutions of this invention may also be mixed with other water-soluble herbicides, for example but not limited to, salts of 2,4-dichlorophenoxyacetic acid, dicamba or 4-chloro-2-methylphenoxyacetic acid, or with finely-divided water-insoluble herbicides, for example but not limited to triazines, substituted ureas, sulfonylureas diphenyl ethers, dinitroanilines, pyridines and the like.

While Roundup® herbicide is the preferred source of a glyphosate water soluble salt, other suitable formulations providing a water soluble glyphosate salt or glyphosate acid may be employed if desired.

Alternatively, the water soluble glyphosate salt or an aqueous solution thereof may be prepared and then added directly as one of the process preparation steps.

Some compositions of the invention were prepared by stirring about a 62 percent by weight aqueous solution of the mono-isopropylamine salt of glyphosate at about room temperature with the desired amount of fatty acid as a potassium salt and optionally, with a saturated solution of ammonium sulfate.

The formulations of the present invention may be conveniently prepared by mixing the desired ingredients together as in a blender or in any suitable container of device producing the needed amount of agitation resulting in mixed ingredients.

Formulation examples were generally prepared by the following process:

(1) adding all or a portion of the desired amount of initial water in a first container, (2) adding a portion of water and potassium hydroxide to the desired amount of fatty acid in a separate container to form a premix, (3) adding the fatty acid containing the potassium hydroxide in the premix from the separate container to the first container containing the initial water, 4) adding a water soluble salt of N-phosphonomethylglycine alone with surfactant to the first container to form a desired final non pH adjusted mixture/solution, 5) adjusting the mixture/solution to a final desired pH by adding appropriate amounts of a concentrated potassium hydroxide solution and thereafter if desired, 6) admixing any remaining water and optional ingredients such as an anti-microbial for example Proxel® GXL (CAS 2634-33-5), sorbic acid, Legend MK, mixtures thereof and the like.

The conversion of a fatty acid such as pelargonic acid to salt such as a potassium salt is the step requiring most scrutiny of the process of this invention.

Pelargonic acid is a thin, clear oil at room temperature which sits on the surface of water when added. With mild agitation, the conversion time to form the salt of the fatty acid is slow. Extreme agitation and long batch stirring time are generally necessary to make the conversion complete which is desired.

In laboratory test batches, preparation of formulations of this invention was generally done by making the fatty acid salt in a separate smaller premix vessel using a beaker and vigorous agitation. This premix was then added to the already mixed ingredients in a larger first container.

As used herein the term "vigorous agitation" includes stirring or mixing by any mechanical or equivalent means to produce a well mixed composition providing thorough blending.

The process of preparing a formulation of this invention may be done at temperatures in the range from about 10° C. to about 100° C. and preferably from about 20° C. to about 40° C.

As another optional ingredient, an anti-foam agent may be included. Various suitable anti-foam agents include SAG 47 which is preferred as an anti-foam agent and Silicone Anti Foam® 30 IND.

The amount of anti-foam agent optionally employed is that which is sufficient to control and reduce an amount of foam which may be formed during the process of preparation of the formulation of this invention to a desired satisfactory level from a user's viewpoint. Generally the concentration of anti-foam agent is in the range from about 0.001% by weight of the total ingredients to about 0.1% although greater or lesser amounts of optional anti-foam agent may be employed.

Alternatively, a premix of about 1 part by weight Roundup® herbicide, about 2 parts water and potassium hydroxide as a 20 percent by weight solution was used to form a premix. Pelargonic acid was blended in this premix but thereafter separated easily. The benefit of this (alternative) process of preparation was that the premix went into the batch water with only mild agitation. Care must be given to prevent possible heat residue in the premix beaker.

The most preferred previously described process requires some agitation. It may be likely that the addition of the fatty acid at the suction side of a flow through homogenizer Tekmar for example, into the potassium hydroxide composition would be sufficient to produce the desired amount of agitation.

In a preferred process for preparing formulations of this invention, the vessel wherein the formulation will be 50 gallons or more is initially charged with about 25% of the total desired water. Gentle agitation or recirculation is begun during and after this initial water addition. A base providing hydroxide in water is added as is optionally an ethoxylated tallowamine surfactant such as Entry II® Surfactant, sold by Monsanto Company, St. Louis, Mo. USA.

Agitation is increased and the added fatty acid is allowed to react. When the reaction is considered complete, the fatty acid appears homogeneous and not aggregated at the surface of the resulting composition. About half of the remaining desired water is added as are desired amounts of the isopropylamine salt of glyphosate, and optionally Proxel and Sag 47 with time allowed for adequate mixing. Thereafter remaining desired water is added and the pH is adjusted using potassium hydroxide.

Ready to use formulations having $C_9$ or $C_{10}$ fatty acids in the range from about 0.5 to about 1% by weight of the total spray weight were the most effective formulations from a herbicidal efficacy viewpoint with mixtures thereof providing similar efficacy.

The formulations of the present invention can be readily used as prepared or further diluted in water by a user in a spray container prior to use, although those of skill in the art will recognize that the dilution will have a practical dilution limit set by efficacy.

Suitable herbicidally efficacious application rates of glyphosate will vary depending on plant species, weather, climate and geography. The spray volume is in the range from about 10 to about 1000 gallons per acre (gpa) preferably from about 50 to about 250 gpa. U.S. Pat. No. 3,799,758 provides illustrative application rates of glyphosate on an acid equivalent basis.

The following examples are presented to illustrate the present invention as well as some of the various embodiments of the invention. These examples are presented as being illustrative of the novel formulations and are not intended to be a limitation of the scope thereof. Rather these examples are intended to teach by illustration and provide what is believed to be a useful and readily understood description of procedures to make and use the invention.

In the examples, all parts, percentages and properties are by weight unless otherwise indicated. In some examples, comparative formulations illustrative of the prior art were made and compared to compositions of this invention.

EXAMPLES

General Methods

Tall fescue, common bermuda, common dandelion, sweet clover and large crabgrass were grown from seed in 4 inch square pots containing a mixture of soil and commercial soil conditioners. After planting, the soil was kept moist and seedlings emerged in 5–8 days. Approximately 2 weeks after emergence, plants were mowed to a uniform height of 6 cm. Height was maintained at 6 cm with 3 mowings per week for fescue, bermuda and crabgrass and with 1 mowing per week for dandelion and clover. Unless otherwise noted, all species except crabgrass were about 8 weeks old at the time of treatment. Crabgrass was 4–5 weeks old. Treatments were applied with a Devilbiss atomizer using compressed air. Chemicals were formulated as described for individual tests. For quick symptom development (1–3 DAT), evaluations were made on a 0–3 scale where 0=no effect 1=injury noticeable compared to untreated control 2=injury obvious 3=injury dramatic Percent control ratings at later time periods were made on a 0–100 scale where 0=no effect and 100 is complete death. Results are the average of 2 replications.

Example 1

Combinations of $C_8$–$C_{12}$ saturated fatty acids as their potassium salt with Gy glyphosate and an ethoxylated tallow amine surfactant having a degree of ethoxylation of about 15 to 18 were prepared.

Eight formulations containing either 0.5% or 1% $C_8$, $C_9$, $C_{10}$ or $C_{12}$ saturated fatty acids in 0.96% glyphosate-IPA and 0.36% ethoxylated tallow amine surfactant were applied respectively at 225, 112 or 56 gallons per acre to 8 week old fescue and bermuda, 5 week old dandelion and sweet clover and 4 week old crabgrass. Visual observations of burndown were made 1 DAT (Day After Treatment) on 0–3 scale and at 26 DAT on 0–100 scale. Results are in Table 1.

Example 2

Efficacy of $C_9$ and $C_{10}$ saturated fatty acids as the potassium salt alone and in mixtures in combinations with glyphosate.

Eight week old tall fescue and bermuda, 4 week old crabgrass and 2 week old yellow nutsedge were sprayed with $C_9$ and $C_{10}$ saturated fatty acids at 0.5 and 1% w/v alone and in mixtures at volumes of 56, 112 and 225 gal/A. Yellow nutsedge had not been mowed prior to spraying. Visual observations of burndown were made on a 0–3 scale 1 DAT and percent control was evaluated on a 0–100 scale 29 DAT. Results are in Table 2.

In Table 2 following $C_9$ and $C_{10}$ fatty acids and mixtures of both give significant enhancement of final control of yellow nutsedge by glyphosate, as indicated. Mixtures appear more potent in this regard than either $C_9$ or $C_{10}$ fatty acid on its own. The fatty acids without glyphosate have zero effect on yellow nutsedge. Yellow nutsedge is a major problem weed and one that is typically difficult to control with glyphosate-based products.

Example 3

Effect of $C_9$ and $C_{10}$ saturated fatty acids as its potassium salt on glyphosate.

Formulations containing 0.96% IPA-glyphosate (0.74% ae) and 0.4% ethoxylated tallow amine surfactant having a degree of ethoxylation of 15 to 18 were prepared as shown in Table 3a. In addition a concentrated formulation containing 16.5% IPA-glyphosate, 6.15% ethoxylated tallow amine surfactant having a degree of ethoxylation of 15 to 18 and 4.1% $C_9$ 4.1% $C_{10}$ fatty acid was diluted and sprayed at the same final concentration of active. Treatments were applied at 56 and 112 gal/A. Visual observations of injury were recorded 1, 3 and 25 days after treatment. Results are shown in Tables 3a and 3b.

Example 4

Use of $C_9$ saturated fatty acid for enhanced burndown with Roundup® LLG ready-to-use herbicide.

Results of treatments of Roundup® LLG ready-to-use herbicide alone and in mixture with $C_9$ saturated fatty acid at 0.5% and at 1.0% of the spray solution are shown in Table 4.

Example 5

The effect of pH adjustment on performance of a mixture of Roundup® LLG ready-to-use herbicide containing 1% $C_9$ saturated fatty acid is shown in Table 5.

Although this invention has been described with respect to specific embodiments, the details hereof are not to be construed as limitations, for it will be apparent that various equivalents, changes and modifications may be resorted to without departing from the spirit and scope of this invention and it is understood that such equivalent embodiments are intended to be included within the scope of this invention.

What is claimed is:

1. An agriculturally acceptable herbicidal aqueous composition providing initial visible symptoms of contact of a fatty acid or fatty acid salt component thereof and longer term herbicidal kill or control by N-phosphonomethylglycine or an N-phosphonomethylglycine salt component thereof, comprising:
   a) N-phosphonomethylglycine or one or more agriculturally acceptable water soluble salts thereof or mixtures thereof or a compound which metabolizes thereto; and
   b) a $C_8$ to $C_{12}$ saturated or unsaturated, straight or branched chain fatty acid or agriculturally acceptable salt thereof or mixture of said $C_8$ to $C_{12}$ fatty acids and salt(s) thereof or mixture of salts of said $C_8$ to $C_{12}$ fatty acid(s)
   said composition having a pH in the range from about 6.4 to about 7.25.

2. The composition of claim 1 wherein the ratio by weight of component a) to component
   b) is in the range of about 1:10 to about 10:1.

3. The composition of claim 1 wherein the ratio by weight of component a) to component
   b) is in the range from about 1:5 to about 5:1.

4. The composition of claim 1 wherein the ratio by weight of component a) to component
   b) is in the range from about 1:3 to about 3:1.

5. The composition of claim 1 wherein said agriculturally acceptable water soluble salt of N-phosphonomethylglycine is the isopropylamine salt of N-phosphonomethylglycine.

6. The composition of claim 1, wherein said agriculturally acceptable water soluble salt of N-phosphonomethylglycine is the trimethylsulfonium salt of N-phosphonomethylglycine.

7. The composition of claim 1, wherein said fatty acid is capric acid or pelargonic acid or a mixture thereof and said fatty acid salt is the potassium salt or salts of said fatty acid.

8. The composition of claim 1, wherein the pH of the composition is in the range from about 6.8 to about 7.0.

9. The composition of claim 1, further comprising a surfactant.

10. The composition of claim 9, wherein said surfactant comprises an ethoxylated tallow amine.

11. The composition of claim 1, wherein said fatty acid(s) and salt(s) thereof are present in a total fatty acid equivalent concentration of about 0.5% to about 1.0% by weight.

12. The composition of claim 9, further comprising an antifoam agent.

13. A method of killing or controlling plants, comprising applying to said plants a herbicidally effective amount of a composition according to any one of claim 2–12.

14. A process for preparing a composition of claim 1 comprising
   (i) adding to water in any order
      a) N-phosphonomethylglycine or an agriculturally acceptable water soluble salt thereof or mixtures thereof or a compound which metabolizes thereto and
      b) at least one $C_8$ to $C_{12}$ saturated or unsaturated, straight or branched chain fatty acid or an agriculturally acceptable salt(s) thereof or mixtures thereof, and
   (ii) adding a base to adjust the pH to within the range from about 6.4 to about 7.25.

15. The process of claim 14 wherein said pH is adjusted to within the range from about 6.8 to about 7.0.

16. The process of claim 14 wherein said base is a hydroxide or an amine.

17. The process of claim 14 wherein said base is an alkali metal or alkaline earth metal hydroxide.

18. The process of claim 14 wherein said base comprises potassium or sodium hydroxide.

19. The process of claim 14 wherein said base comprises potassium hydroxide.

20. A method of killing or controlling plants comprising applying to said plants a herbicidally effective amount of an aqueous composition providing initial visible symptoms of contact of a fatty acid or fatty acid;. salt component thereof and longer term herbicidal kill of control by N-phosphonomethylglycine or an N-phosphonomethylglycine salt component thereof, wherein the composition comprises N-phosphonomethylglycine or one or more agriculturally acceptable water soluble salts thereof or mixtures thereof or a compound which metabolized thereto and a $C_8$ to $C_{12}$ saturated or unsaturated, straight or branched chain fatty acid or agriculturally acceptable salt thereof or mixture of fatty acids and salt(s) thereof or mixture of salts of fatty acid(s). said composition having a pH in the range from about 6.4 to about 7.25.

21. A process of preparing a agriculturally acceptable herbicidal aqueous composition providing initial visible symptoms of contact of a fatty acid or fatty acid salt component thereof and longer term herbicidal kill or control by N-phosphonomethylglycine or an N-phosphonomethylglycine salt component thereof comprising:
   (i) adding a portion of the desired amount of water in a first container;
   (ii) adding water and potassium hydroxide to the desired amount of fatty acid in a separate container from the first container to forth a premix, wherein said fatty acid is a $C_8$ to $C_{12}$ saturated or unsaturated, straight or branched chain fatty acid or agriculturally acceptable salt thereof or mixture of said $C_8$ to $C_{12}$ fatty acids mind salt(s) thereof or mixture of salts of said $C_8$ to $C_{12}$ fatty acid(s),
   (iii) adding said premix to the water in said first container to form a diluted premix;
   (iv) adding N-phosphonomethylglycine or a water-soluble salt of N-phosphonomethylglycine or mixtures thereof to the diluted premix to form a non-adjusted mixture; and
   (v) adjusting the pH of said non-adjusted mixture to a final pH of 6.4 to 7.25 by adding an appropriate amount of a potassium hydroxide solution.

22. The process of claim 21 which comprises the additional step of admixing any remaining water and optional ingredients.

* * * * *

UNITED STATES PATENT AND TRADEMARK OFFICE
CERTIFICATE OF CORRECTION

PATENT NO. : 6,468,944 B1
DATED : October 22, 2002
INVENTOR(S) : M. Wayne Bugg, Kristin A. Arnold and Randall J. White It is certified that error appears in the above-identified patent and that said Letters Patent is hereby corrected as shown below:

Column 10,
Line 16, after "acid" delete ";.".
Line 23, replace "metabolized" with -- metabolizes --.
Line 34, after "thereof" insert -- , --.
Line 40, replace "forth" with -- form --.
Line 44, replace "mind" with -- and --.

Signed and Sealed this

Twenty-eighth Day of January, 2003

JAMES E. ROGAN
*Director of the United States Patent and Trademark Office*